United States Patent
Lai et al.

(10) Patent No.: US 8,863,577 B2
(45) Date of Patent: Oct. 21, 2014

(54) ABSORPTION TARGET FOR MEASURING POWER OF HIGH-INTENSITY FOCUSED ULTRASOUND

(75) Inventors: Qiji Lai, Jiangsu (CN); Ninglei Lai, Jiangsu (CN); Guogan Xiong, Jiangsu (CN); Kefan Liu, Jiangsu (CN)

(73) Assignee: Nanjing Haike Medical Equipment Co., Ltd., Jiangsu (CN)

( * ) Notice: Subject to any disclaimer, the term of this patent is extended or adjusted under 35 U.S.C. 154(b) by 348 days.

(21) Appl. No.: 13/508,510

(22) PCT Filed: Jan. 30, 2011

(86) PCT No.: PCT/CN2011/070816
§ 371 (c)(1),
(2), (4) Date: May 7, 2012

(87) PCT Pub. No.: WO2011/103780
PCT Pub. Date: Sep. 1, 2011

(65) Prior Publication Data
US 2012/0222486 A1    Sep. 6, 2012

(30) Foreign Application Priority Data
Feb. 26, 2010 (CN) .......................... 2010 1 0115001

(51) Int. Cl.
*G01H 3/10* (2006.01)
*G01H 17/00* (2006.01)
*A61N 7/02* (2006.01)

(52) U.S. Cl.
CPC . *G01H 17/00* (2013.01); *A61N 7/02* (2013.01)
USPC .......................................................... 73/649

(58) Field of Classification Search
USPC .......................................... 73/649, 1.83, 646
See application file for complete search history.

(56) References Cited

U.S. PATENT DOCUMENTS

| 2,874,794 | A |   | 2/1959 | Kiernan |
| 3,915,017 | A | * | 10/1975 | Robinson ........................ 73/646 |
| 4,181,004 | A | * | 1/1980 | Dominy et al. ................ 73/1.83 |
| 4,625,542 | A | * | 12/1986 | Nelson ............................ 73/1.83 |
| 6,264,607 | B1 | * | 7/2001 | Goll et al. ..................... 600/437 |
| 6,488,639 | B1 | * | 12/2002 | Ribault et al. .................... 601/2 |

FOREIGN PATENT DOCUMENTS

| CN | 1057107 A | 12/1991 |
| CN | 2394209 Y | 8/2000 |
| CN | 2653506 Y | 11/2004 |
| DE | 198 36 727 A1 | 2/2000 |

* cited by examiner

*Primary Examiner* — J M Saint Surin
(74) *Attorney, Agent, or Firm* — Christensen Fonder P.A.

(57) ABSTRACT

An absorption target for measuring power of high-intensity focused ultrasound, comprising a container and a cone target cluster. The cone target cluster includes basic units with the same geometrical shape. The upper part of each basic unit is a pyramid, and the lower part of each basic unit is a prismatic base. The vertexes of respective side surfaces of the pyramid converge at a perpendicular bisector of the prismatic base to form a cone vertex and the cross sections of the pyramid and the base are squares, regular triangles or regular hexagons. The bases of the basic units are seamlessly and tightly arrayed at the bottom in the container. Sound waves of an incident cone target cluster to escape into space outside the cone target cluster only in case of at least two reflections or scatterings. Open micropores are densely distributed inside the basic units of the cone target cluster.

4 Claims, 2 Drawing Sheets

ABSORPTION TARGET FOR MEASURING POWER OF HIGH-INTENSITY FOCUSED ULTRASOUND

PRIORITY CLAIM

The present application is a National Phase entry of PCT Application No. PCT/CN2011/070816, filed Jan. 30, 2011, which claims priority from Chinese Application 201010115001.2, filed Feb. 25, 2010, the disclosures of which are hereby incorporated by reference herein in their entirety.

FIELD OF THE INVENTION

The present invention relates to an absorption target for measuring power of ultrasound up to 1,000 W or above, in particular to an absorption target for measuring power of high-intensity focused ultrasound (HIFU) up to 1,000 W or above.

BACKGROUND OF THE INVENTION

High-intensity focused ultrasound (HIFU) is mainly used for treatment of malignant tumors. It has many clinical features: it can realize noninvasive or minimally invasive surgery; it has more sensitive destruction effects on anaerobic tumor cells; it has indiscriminate treatment effects for proliferative and non-proliferative tumors (liver tumors and kidney tumors, etc.), and can induce specific immune responses of the body against tumors. However, the existing HIFU technique encounters a bottleneck problem when it is used to treat deep seated tumors, infracostal hepatic tumors, and large tumors. It is not because that the HIFU can't achieve high intensity focused ultrasound. For example, when the working frequency of HIFU is f=1.5 MHz, only sound power $P_{40} \approx 150$ (W) is required to obtain focused sound intensity $I_{F0} \approx 15,000$ W/cm$^2$ in a free sound field. However, owing to the natural thermal conductivity and blood supply of human body's tissues, the target area dissipates heat as the HIFU heats up.

From the mean parameters of known acoustical and biophysical of human body's soft tissues, it is easy to know (by means of experimentation and computer simulation) that the mean maximum effective therapeutic depth (maximum focus-skin distance) of niduses in subcutaneous soft tissues by HIFU is only several centimeters. In addition, the treatment speed is very low. Even for a medium-size nidus, the time required for treatment is intolerable. Doing research on a technique that can reliably emit KW-level HIFU with dominant focus performance is a key for truly achieving the "one-off noninvasive surgery" concept with HIFU. Therefore, the measurement of KW-level ultrasound power is an indispensable and key link for research and development, production, actual application, detection and diagnosis, and maintenance of high-intensity focused ultrasound (HIFU) equipment.

With reference to relevant literature, Nanjing HAIKE Medical Equipment Co., Ltd. designed a coeloconoid reflection target that is made of metal materials and can measure KW-level HIFU power. Experiments have shown that such reflection targets can't ensure the sound beams emitted by HIFU transducers with different physical structures meet necessary total internal reflection conditions of longitudinal and transverse waves at the target; therefore, the authenticity is surely doubtful if the sound power of the radiation source is calculated from the measured sound radiation power.

At present, most methods used domestically and abroad for measuring power of high-power and high-intensity focused ultrasound calculate the sound power emitted from the sound source by measuring the normal radial force which acts on the absorption target, so does the method recommended in the national standard of China (GB/T19890-2005). However, at present, only absorption targets for measuring sound power at 100 W level are practical, and they can't meet the present and future demand for HIFU.

SUMMARY OF THE INVENTION

The object of the present invention is to provide an absorption target that can measure power of KW-level high-intensity focused ultrasound, and to overcome the drawback of low upper limit of sound power measurable in existing absorption targets for high-intensity focused ultrasound (HIFU) measuring devices.

The object of the present invention is attained as follows: an absorption target for measuring power of high-intensity focused ultrasound, comprising a container and a cone target cluster submerged in a liquid medium, wherein, the cone target cluster consists of basic units with the same geometrical shape; the upper portion of the basic unit is a pyramid, and the lower portion is a corresponding prismatic base, the vertexes of respective side surfaces of the pyramid converge at a perpendicular bisector of the prismatic base to form a cone vertex, and the cross sections of the pyramid and base are squares, regular triangles, or regular hexagons; the bases of the basic units are seamlessly and tightly arrayed at the bottom in the container; it may be possible for sound waves of an incident cone target cluster to escape into space outside of the cone target cluster only in case of at least two reflections or scatterings.

Open micropores are densely distributed inside the basic units of the absorption target.

In the present invention: the basic material for making the basic units is an inorganic solid material with open micropores; the basic material for making the container is an inorganic solid material with high thermal conductivity.

In the present invention, the basic material for making the basic units is an inorganic solid material which is available in the market, or a specially made simplex or complex inorganic solid material with open micropores, preferably bricks, or stones with open micropores, or rocks with open micropores, or graphite; preferably, the basic material for making the container is metal or glass.

In the present invention: the liquid medium used for the absorption target is deaerated water; the prismatic bases of the basic units are designed in appropriate height such that the sound attenuation is >20 dB; the minimum size of overall bottom of the cone target cluster should be at least 1.5 times of the width of −26 dB sound beam to be intercepted.

The advantages of the present invention include: since a cone target cluster is used, superior physical properties, with a reflection coefficient below −30 dB, can be obtained easily; since the basic material thereof is an inorganic solid material, which is preferably bricks, or stones with open micropores, or rocks with open micropores, or graphite, with properties such as high specific heat, low heating speed, low expansion rate, and zero radiolysis or degeneration under high-dose sound radiation, etc.; therefore, the cone target cluster can be used to measure the power of KW-level focused ultrasound, with stable performance and long service life.

In the figures: 1. Basic Unit, 2. Container, 3. Pyramid, 4. Prismatic Base, 5. Cone Target cluster, 6. Transducer, 7. Counterpoised Electronic Balance, 8. Ultrasound Power Absorption Plate, 9. Ultrasound RF Source, 10. Frequency Meter The Figures illustrate the basic structure of an embodiment of the present invention without limitation; the embodiment of the present invention will be further detailed below, with reference to the Figures.

DETAILED DESCRIPTION

Figure 1:
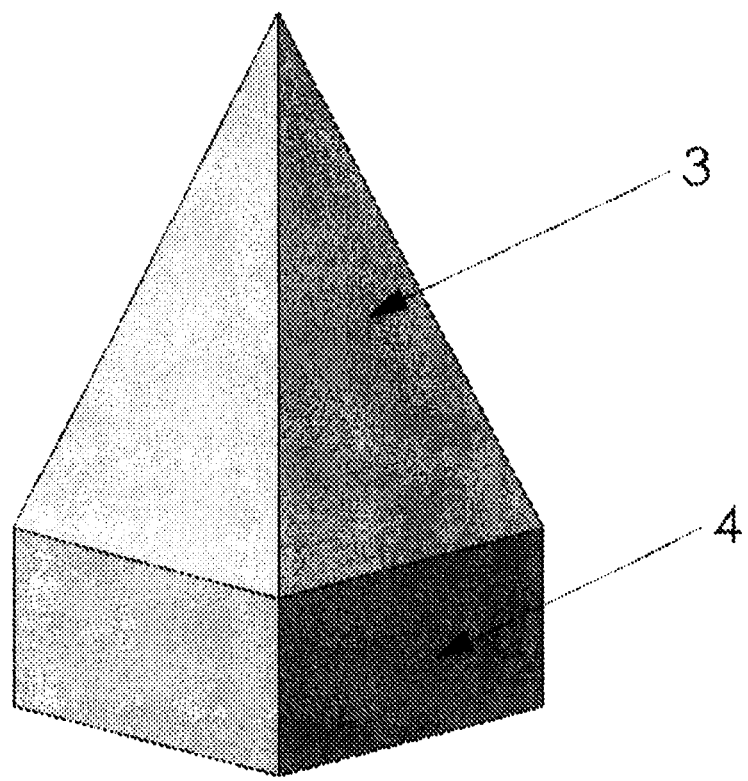
FIG. 1 is a structural schematic diagram of the basic unit of the cone target cluster according to the present invention.
Figure 2:
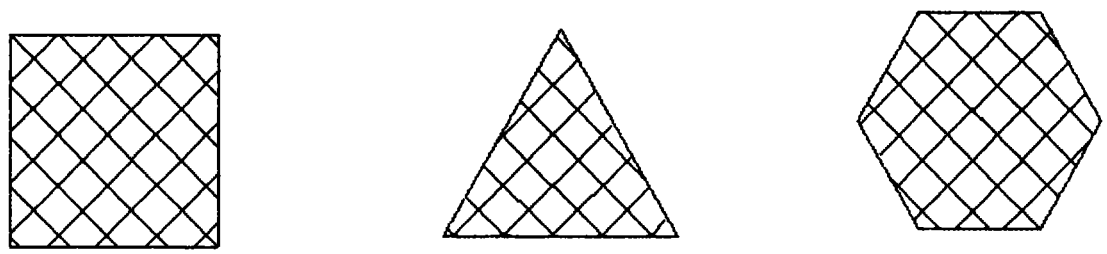
FIG. 2 illustrates several cross-sections geometrical shape of the basic unit of the cone target cluster.

As shown in FIG. 1, in the cone target cluster provided in the present invention, the upper portion of basic unit 1 is a pyramid 3, and the lower portion of basic unit 1 is a prismatic base 4. As shown in FIG. 2, the cross section of basic unit 1 can be: a: square, or b: regular triangle, or c: regular hexagon; the minimum size of the overall minimum bottom (Wmin) of the cone target cluster should be at least 1.5 times the width of −26 dB sound beam to be intercepted, and the prismatic base 4 should be in appropriate height such that the sound attenuation is >20 dB; the vertexes of respective side surfaces of the pyramid 3 converge at the bottom center of basic unit 1 at the perpendicular bisector to form a cone vertex. Open micropores are densely distributed inside the basic unit 1.

Figure 3:
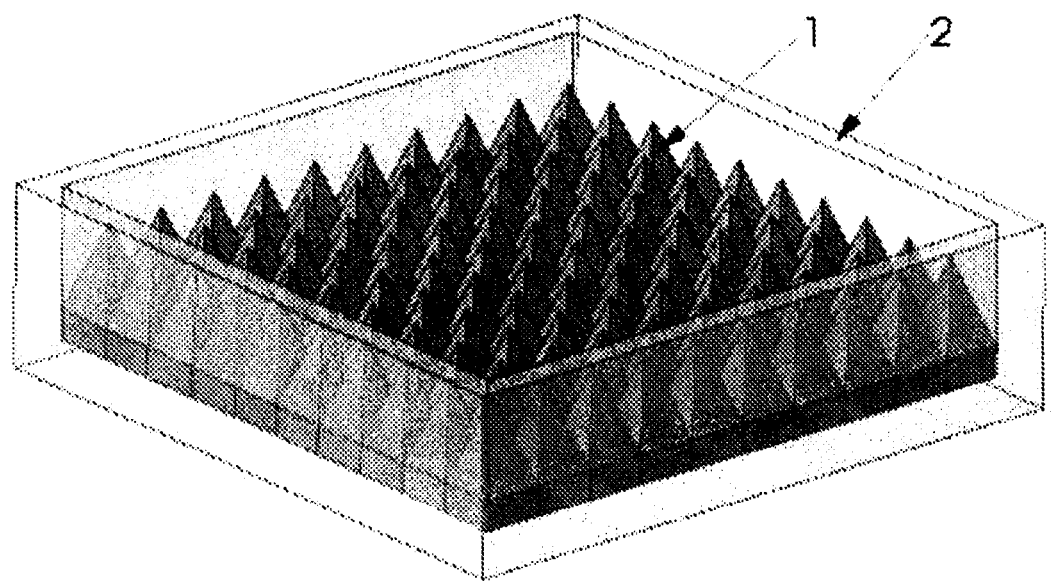
FIG. 3 is a structural schematic diagram of the cone target cluster according to an embodiment of the present invention.

As shown in FIG. 3, the prismatic base 4 of each basic unit 1 is seamlessly and tightly arrayed inside the rectangular container 2 to form a cone target cluster; it may be possible for sound beam of an incident cone target cluster from cone vertex to cone bottom to return to space outside of the target only in case of at least two reflections or scatterings.

In actual implementation, for example, the basic unit 1 should be made of an inorganic solid material with high thermal conductivity and low sound pressure reflection coefficient between it and the liquid medium for the absorption target; the rectangular container should be made of an inorganic solid material with high thermal conductivity.

Structure and working conditions of the cone target cluster are described further below.

Selection of the inorganic solid material for making the basic units of the cone target cluster: Praguite 06 bricks (refractory bricks) from Yixing Shengde Ceramics Co., Ltd.

In the cone target cluster, the base height of the basic units is 25 mm, and the cross section is a square with 16 mm side length, and the height from the vertex of the pyramid to the upper surface of the base is 30 mm.

The inorganic solid material for making the rectangular container is glass. The cubic capacity of the container is 256 mm×256 mm×60 mm (L×W×D).

The basic units are seamlessly and tightly arrayed in 16 rows×16 columns in the rectangular container.

Working conditions of the absorption target: the liquid medium is deaerated water; the maximum measurable sound power is no less than 3,000 W.

The method is: The cone target cluster 5 is submerged in the liquid medium before testing, t, and the air entrapped in the micropores of the cone target cluster is removed under A vacuum state, so that the open micropores densely distributed inside the basic units of the cone target cluster 5 are filled with the liquid medium.

Figure 4:
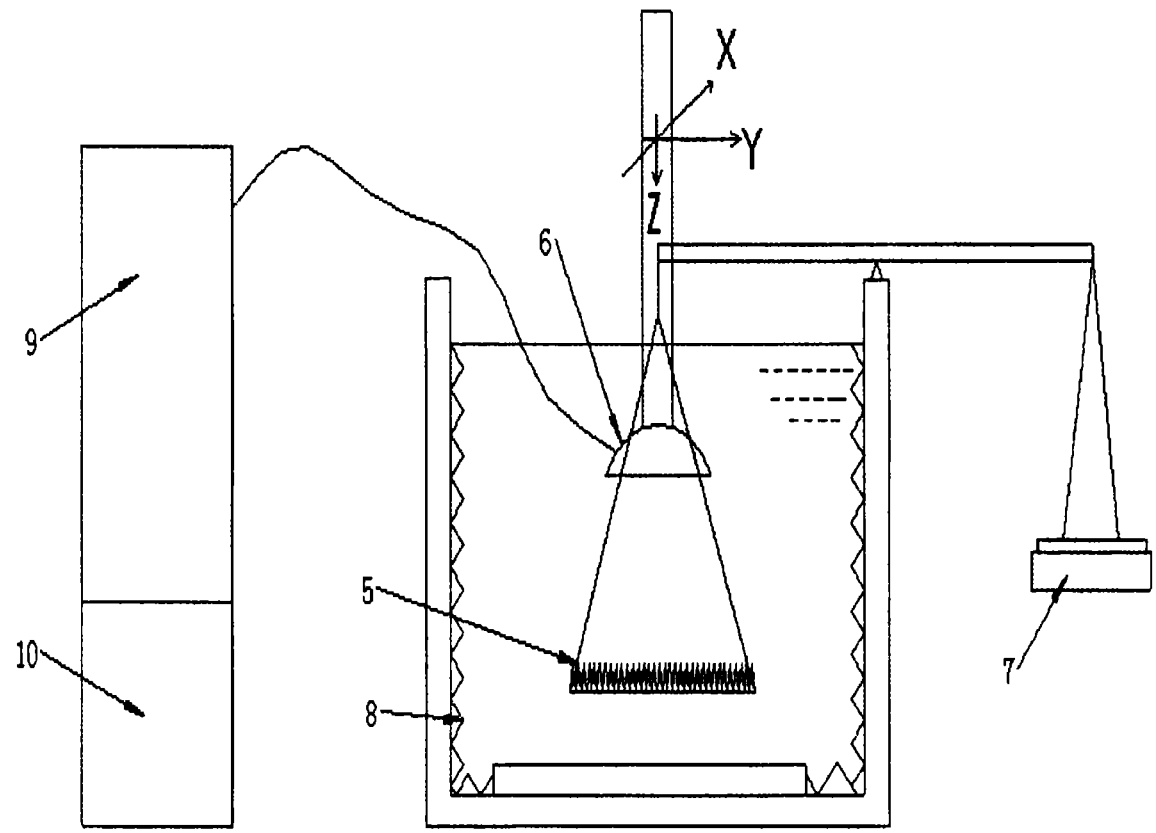
FIG. 4 shows a radial force balance measurement system that utilizes the HIFU transducer in the present invention for measuring power of HIFU.

The ultrasound radiation force measuring device is shown in FIG. 4. The ultrasonic source should be fixed to a precision 3D motion platform, and the absorption target is suspended by a counterpoised electronic balance 7 via a lever mechanism under a transducer 6, and the sound beam axis of the ultrasonic source should be parallel with the plumb line of the absorption target. In addition, ultrasound power absorption plates 8 should be mounted on the inner walls of the ultrasound radiation force measuring device. The axial position of the absorption target should be offset from the sound focus and near the sound source to avoid the adverse effect of nonlinearity and sound stream to the measurement of radial force. The bottom plane of the absorption target should be perpendicular to the sound beam axis, the center of the absorption target should be aligned to the sound beam axis, and the distance to the transducer 6 or the surface center of transducer 6 should be less than 0.7 times of the focal length under the sound pressure. Before measurement, the absorption target should be submerged in deaerated water and deaerated for 30 minutes or more. Under vacuum, and the instrument should be warmed up for 15 minutes or more.

To reduce the effect of thermal drift, the short-time (2~4 s) stable values indicated on the counterpoised electronic balance 7 should be taken when the ultrasound pressure is applied and when the ultrasound pressure is interrupted; the difference between the two values is the ratio m of normal radial force F suffered by the cone target cluster to gravitational acceleration g, in units of kg.

If a lever mechanism is used, the force measured by the counterpoised electronic balance 7 should be converted to the actual force suffered by the absorption target by calibrating the moment arm ratio.

The surfaces of cone target cluster 5 and transducer 6 should be observed from time to time, and any small bubbles on the surfaces should be removed timely in the measurement process.

Calculation of ultrasound power (with the sound attenuation effect of the deaerated water neglected) is described below.

When a spherical segment focused unit transducer with a round hole in the center is used as the sound source, the sound power can be calculated as follows:

$$P = \frac{2FC}{\cos\beta_1 + \cos\beta_2} \quad (C.1)$$

Wherein, P—Sound power, unit: W;

C—Sound beam speed in water, unit: m/s;

F—Normal radial force suffered by the absorption target, unit: N;

$\beta_1$—Half convergence angle of the spherical segment focused transducer at the outer aperture, unit: °;

$\beta_2$—Half convergence angle of the spherical segment focused transducer at the center hole, unit: °.

The expression C.1 can be used if a spherical cap focused unit transducer without center hole is used as the sound source, with cos $\beta_2$=1.

The present invention is not limited to the above embodiment. In particular, in the absorption target, the cone target cluster 5 is mainly made of an inorganic solid material which is available in the market or a special made simplex or complex inorganic solid material with open micropores, preferably bricks, or stones with open micropores, or rocks with open micropores, or graphite; preferably, the basic material for making the container is metal or glass.

The invention claimed is:

1. An absorption target for measuring power of high-intensity focused ultrasound, comprising a container and a cone target cluster submerged in a liquid medium, wherein, the cone target cluster comprises basic units with the same geometrical shape; the upper portion of the basic unit is a pyramid, and the lower portion is a corresponding prismatic base, vertexes of respective side surfaces of the pyramid converge at a perpendicular bisector of the prismatic base to form a cone vertex, and cross sections of the pyramid and the base are squares, regular triangles, or regular hexagons; the bases of the basic units are seamlessly and tightly arrayed at the bottom of the container; it may be possible for sound waves of an incident cone target cluster to escape into space outside the cone target cluster only in case of at least two reflections or scatterings and open micropores are densely distributed inside each of the basic units of the cone target cluster.

2. The absorption target for measuring power of high-intensity focused ultrasound according to claim 1, wherein a basic material for making the basic units is an inorganic solid material with open micropores; and a basic material for making the container is an inorganic solid material with high thermal conductivity.

3. The absorption target for measuring power of high-intensity focused ultrasound according to claim 2, wherein a basic material for making the basic units are bricks, or stones with open micropores, or rocks with open micropores, or graphite and a basic material for making the container is metal, or glass.

4. The absorption target for measuring power of high-intensity focused ultrasound according to claim 1, wherein the liquid medium used for the absorption target is water, and the prismatic base of the basic units comprise a height such that a sound attenuation is >20 dB; the minimum size of the overall bottom of the cone target cluster should be at least 1.5 times of the width of −26 dB sound beam to be intercepted.

* * * * *